United States Patent [19]

Warren et al.

[11] 4,238,495
[45] Dec. 9, 1980

[54] 1-(4-CYANO-PHENOXY)-2-HYDROXY-3-[2-(5-1H-TETRAZOLYL)-CHROMON-5-YLOX-Y]-PROPANE AND SALTS THEREOF

[75] Inventors: Brian T. Warren, Ickenham; John W. Spicer, Booker, both of England

[73] Assignee: Miles Laboratories, Inc., Elkhart, Ind.

[21] Appl. No.: 653,744

[22] Filed: Jan. 30, 1976

Related U.S. Application Data

[63] Continuation-in-part of Ser. No. 419,809, Nov. 28, 1973, abandoned.

[51] Int. Cl.³ .................... A61K 31/41; C07D 257/04

[52] U.S. Cl. ........................ 424/269; 548/253
[58] Field of Search .............. 260/308 D; 424/269

[56] References Cited

U.S. PATENT DOCUMENTS 3,882,148   5/1975   Augstein et al. .............. 260/308 D

*Primary Examiner*—Frederick E. Waddell
*Attorney, Agent, or Firm*—James D. McNeil

[57] ABSTRACT

1-(4-Cyano-phenoxy)-2-hydroxy-3-[2-(5-1H-tetrazolyl)-chromon-5-yloxy]-propane and its pharmacologically acceptable salts, are useful in the treatment of allergies, allergic asthma and inflammation.

6 Claims, No Drawings

1-(4-CYANO-PHENOXY)-2-HYDROXY-3-[2-(5-1H-TETRAZOLYL)-CHROMON-5-YLOXY]-PROPANE AND SALTS THEREOF

REFERENCE TO PRIOR APPLICATION

This is a continuation-in-part of U.S. patent application Ser. No. 419,809, filed on Nov. 28, 1973 now abandoned.

BACKGROUND OF THE INVENTION

1. Field of the Invention

This invention relates to pharmacologically active compounds useful in the treatment of allergic and inflammatory conditions, particularly allergic asthma and hay fever. Those compounds are classifiable in U.S. Classes 260/308D and 260/345.2 and in International Class C07d 7/34.

2. Description of the Prior Art

U.S. Pat. No. 3,882,148 (5/75; "Augstein") discloses a genus of compounds having the structure,

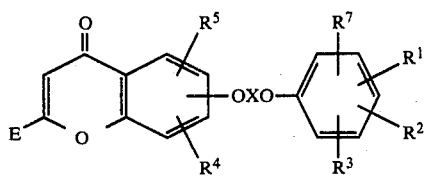

(I)

in which: each of substituents $R^1$-$R^5$ and $R^7$ can be a hydrogen atom, a hydroxyl, alkoxyl, benzyloxyl, acyl, amino, acylamino, alkenyl, halogeno, or an alkyl group; X can be a hydrocarbon chain of from 2 to 10 carbon atoms optionally substituted by a hydroxyl group; and E can be a tetrazolyl or carboxyl group.

Because I contains structural features not germane to the present invention, it is convenient to simplify that formula to compounds having structure I or Ia in which R is a cyano group.

Augstein discloses that compounds having structural formula I are useful in the treatment of disorders in which SRS-A (slow reacting substance of anaphylaxis) is a factor, such as asthma, hay fever, skin disorders and diseases of the respiratory system.

U.S. Pat. No. 3,899,513 (8/75; "Warren") describes compounds having the structure,

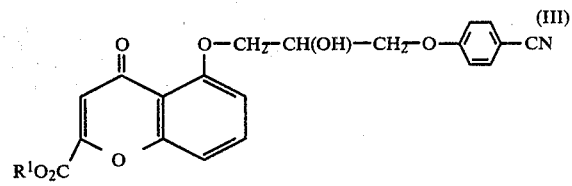

(III)

in which: $R^1$ can be a hydrogen atom, a nontoxic cation, or an alkyl group of 1 to 4 carbon atoms. Compounds III are useful as starting materials for those disclosed in this specification. Warren teaches that compounds III are useful in the treatment of allergic conditions.

Example 5 of this specification demonstrates that the claimed compounds have therapeutic indices superior those of compounds Ia and III.

SUMMARY OF THE INVENTION

The subject matter of this invention includes: 1-(4-cyano-phenoxy)-2-hydroxy-3-[2-(5-1H-tetrazolyl)-chromon-5-yloxy]-propane and its pharmacologically acceptable, non-toxic salts; a process for preparing that compound; intermediates that are useful in the process; and a therapeutic method of producing an anti-allergic effect in mammals or in man utilizing 1-(4-cyano-phenoxy)-2-hydroxy-3-[2-(5-1H-tetrazolyl)-chromon-5-yloxy]-propane and its salts.

1-(4-Cyano-phenoxy)-2-hydroxy-3-[2-(5-1H-tetrazolyl)-chromon-5-yloxy]-propane has the structure,

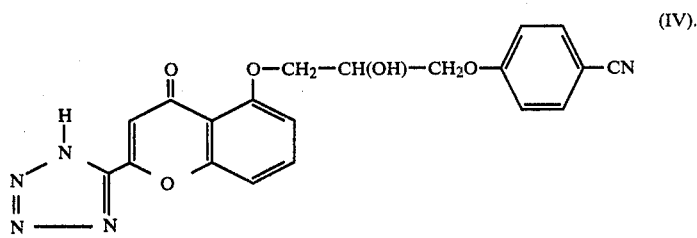

(IV).

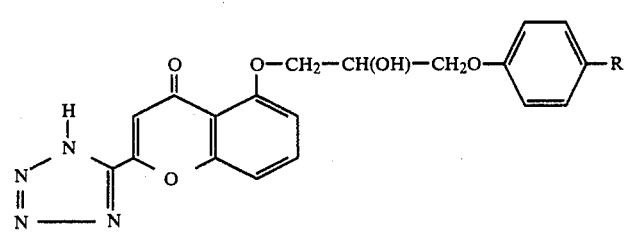

(Ia)

in which R can be a hydrogen atom, a halogeno, hydroxyl, or an alkyl group. While Augstein does not provide specific examples of Ia, that reference nevertheless provides generic disclosure of those compounds. The disclosure in Augstein, however, does not include Pharmacologically acceptable, non-toxic salts of IV include, for example, the sodium, dimethylaminoethanol, and trishydroxymethylaminomethane salts.

Compound IV is prepared by the following process:

(1) reacting 1-(4-cyano-phenoxy)-2-hydroxy-3-(2-carbalkoxychromon-5-yloxy)-propane,

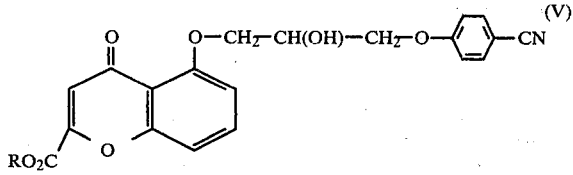

(V)

in which R is an alkyl group of from 1 to 4 carbon atoms, with ammonia in a solvent such as ethanol, chloroform, or a chloroform/ethanol mixture, at from −5%C. to 10° C. to obtain the corresponding amide, 1-(4-cyano-phenoxy)-2-hydroxy-3-(2-amido-chromon-5-yloxy)-propane,

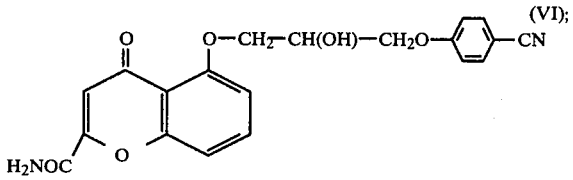

(VI);

(2) dehydrating the amide at a temperature of from 40° C. to 60° C. with a reagent mixture such as p-toluenesulfonyl chloride/pyridine, p-toluenesulfonyl chloride/colidine, or p-toluenesulfonyl chloride/lutidine in dimethylformamide to obtain the corresponding nitrile, 1-(4-cyano-phenoxy)-2-formyloxy-3-(2-cyano-chromon-5-yloxy)-propane:

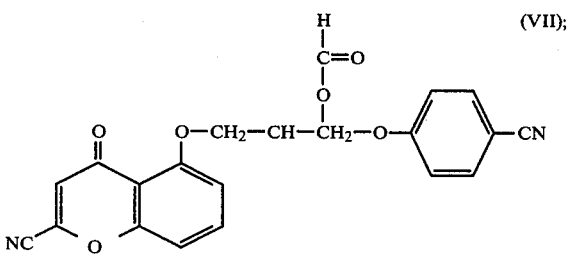

(VII);

(3) reacting the nitrile with sodium azide and ammonium or sodium chloride in an organic solvent such as dimethylformamide, dimethylsulfoxide, or dimethylacetamide to obtain a corresponding salt of a tetrazolyl derivative,

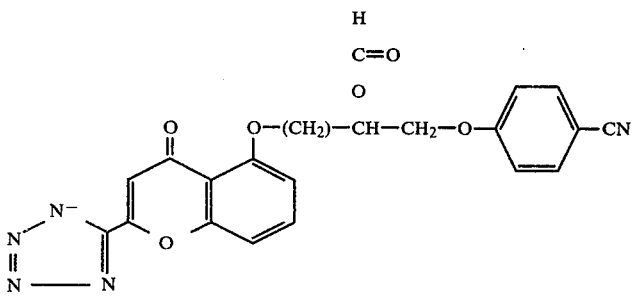

wherein X is a sodium, or ammonium cation; and, (4) treating the tetrazolyl derivative with a dilute mineral acid to acidify the salt and to hydrolyze the formyl group thereof to obtain compound IV.

Step (3) of the process optionally may be carried out with an alkali-metal azide such as sodium, potassium, or lithium azide without ammonium or sodium chloride; in that case, $X^+$ in VIII is a sodium, potassium, or lithium cation.

Starting materials V are prepared as follows:

(1) reacting 2,6-dihydroxyacetophenone,

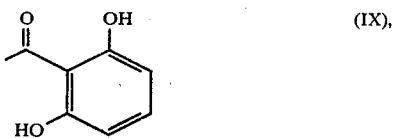

(IX), with 4-cyanophenylglycidyl ether,

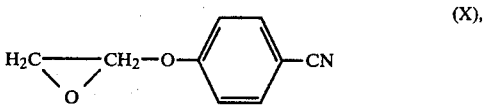

(X), in 2-ethoxyethanol in the presence of benzyltrimethylammonium hydroxide to obtain a bis-(substituted-phenoxy)-propane,

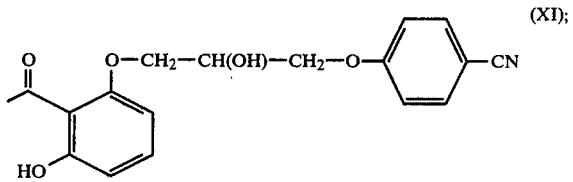

(XI);

(2) recovering the (bis-phenoxy)-propane and reacting it with diethyl oxalate to obtain an intermediate,

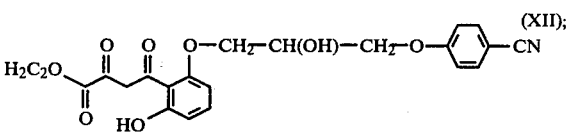

(XII);

(3) recovering the intermediate and reacting it with a cyclization mixture such as concentrated hydrochloric acid and a lower alcohol of 1 to 4 carbon atoms, thus obtaining compound IV. Details of the preceding synthesis are available in Warren (U.S. Pat. No. 3,899,513).

1-(4-Cyano-phenoxy)-2-hydroxy-3-(2-amido-chromon-5-yloxy)propane (VI) and 1-(4-cyano-phenoxy)-2-formyloxy-3-(2-cyano-chromon-5-yloxy)-propane are key intermediates in the synthesis of compound IV.

Compound IV and its non-toxic salts possess antiallergic properties that make them useful in treating allergic, asthmatic, and certain inflammatory conditions; those compounds may also be useful in treating autoimmune diseases. An anti-allergic effect is produced in an individual in need of such therapy by administration of an effective amount of compound IV or a pharmacologically acceptable salt thereof. The term "individual" means a human being or an experimental animal used as a model thereof. The compounds may be administered by inhalation, injection, ingestion, or other suitable routes of administration. Effective doses range from 0.075 to 2.25 μmole/kg. Succeeding example 5 provides details of the method.

Compound IV and its salts also have anti-inflammatory activity upon topical application to inflamed areas of the skin or of the eye.

For the treatment of asthma, compound IV or a salt thereof may be in a form suitable for administration by inhalation. That form can comprise a suspension or solution of the active ingredient in water or in a suitable alcohol for administration as an aerosol by means of a conventional nebulizer. Alternatively, that form can comprise a suspension or solution of the active ingredient in a conventional liquefied propellant to be administered as an aerosol from a pressurized container. The forms for administration can comprise the solid active ingredient in a solid diluent for administration from a powder inhalation device. Other routes of administration: e.g. sublingual, oral or buccal tablets; rectal suppositories; parenteral injection; or intravenous infusion; can also be used.

The form for administration can also contain, in addition to compound IV, other active bronchodilating ingredients, e.g. those of the β-adrenergic type, such as iso- or orciprenaline or salbutamol. The forms for administration can contain 0.1 to 10% by weight of compound IV or a salt thereof. If salbutamol or iso- or orci-prenaline sulphate are used, they are suitably present in a concentration of 0.1 to 5% by weight.

DESCRIPTION OF THE PREFERRED EMBODIMENTS

Example 1

1-(4-CYANO-PHENOXY)-2-HYDROXY-3-(2-AMINO-CHROMON-5-YLOXY)PROPANE (MONOHYDRATE)

In a 12 L, 3-necked flask equipped with stirrer, thermometer and gas-inlet tube were placed 832 g (2.03 moles) of 1-(4-cyano-phenoxy)-2-hydroxy-3-(2-carbethoxychromon-5-yloxy) propane, 3.7 L of chloroform and 3.3 L of 95% ethanol. The slurry was warmed to 35° C. to obtain a clear solution. The solution was then slowly cooled to 10° C. while ammonia gas was introduced into the solution at a rapid rate and kept at 10° C. until it was saturated with ammonia. The solution again was cooled and kept at 0°–5° C. while ammonia was being introduced (at a slower rate) for an additional 4–6 hours. The resulting precipitate was collected by filtration, washed with ethanol and then with ether: 695 g (86% yield); m.p. 203°–204° C.

Analysis: Calculated for $C_{20}H_{16}N_2O_6 \cdot H_2O$: C, 60.30; H, 4.56; N, 7.03. Found: C, 60.55; H, 4.34; N, 7.01. TLC $R_f=0.22$ (toluene-ethyl formate-formic acid 4:5:1).

Example 2

1-(4-CYANO-PHENOXY)-2-FORMYLOXY-3-(2-CYANO-CHROMON-5-YLOXY)PROPANE (MONOHYDRATE).

In a 12, 3-necked flask equipped with a stirrer and thermometer were placed 1945 g of p-toluenesulfonyl chloride, 1945 g of pyridine and 1690 ml of dimethylformamide (DMF). The solution was stirred while 695 g (1.745 moles) of 1-(4-cyano-phenoxy)-2-hydroxy-3-(2-amidochromon-5-yloxy)-propane (monohydrate) were added portionwise, keeping the temperature between 50°–60° C. with the aid of a cold water bath. The addition required about 30 min. After being stirred and heated at 50°–55° C. for an additional 1 hour, the reaction mixture was cooled to 25° C., and 5 L of chloroform was added. The dark solution was then poured into 5 L of ice-water and made acid with 530 ml of concentrated hydrochloric acid. The chloroform layer was separated and washed twice with 2 L portions of water. After stripping off the solvent on a rotary evaporator, the residue was slurried in 4.0 L of ethanol. The product was collected by filtration, washed with ethanol, and then with ether: 565 g (80% yield); m.p. 153°–154° C.

Analysis: calculated for $C_{21}H_{14}N_2O_6 \cdot H_2O$: C, 61.76; H, 3.95; N, 6.86. Found: C, 61.63; H, 3.41; N, 6.73. TLC $R_f=0.58$ (toluene-ethyl formate-formic acid 5:4:1).

Example 3

1-(4-CYANO-PHENOXY)-2-HYDROXY-3-[2-(5-1H-TETRAZOLYL)CHROMON-5-YLOXY]-PROPANE

In a 5 L three-necked flask equipped with a stirrer, thermometer, and reflux condenser were placed 565 g (1.38 moles) of 1-(4-cyanophenoxy)-2-formyloxy-3-(2-cyanochromon-5-yloxy)propane (monohydrate), 153 g of sodium azide, 119 g of ammonium chloride and 2.8 L of DMF. The mixture was stirred and heated at 90° C. for 3 hours.

The reaction mixture was then stripped of DMF on a rotary evaporator. The residue was dissolved in 4.5 L of acetone and 450 ml of water; 50 ml of concentrated sulfuric acid was added, the solution stirred, and refluxed for 1 hour.

An additional 2.5 L of water was added to the hot solution. The acetone was removed by distillation until the internal temperature reached 80° C. The reaction mixture was then stirred at room temperature overnight.

The product was collected by filtration and washed with water: 525 g; m.p. 219°–221° C.

The crude material was dissolved in a hot solution of 5.25 L of dioxane and 1.05 L of water. After treatment with activated charcoal and filtration, the filtrate was stripped of solvent on a rotary evaporator keeping the temperature below 40° C. The residue was slurried in 2.5 L of hot methanol and then cooled in an ice-bath. The light cream-colored solid was collected by filtration and washed with cold methanol. After drying at 60° C. the solvated material was slurried in 2.0 L of toluene and slowly heated to boiling. After boiling for 10–15 minutes, the product was collected by filtration; 441 g (80° yield); m.p. 223° C.

Analysis: calculated for $C_{20}H_{15}N_5O_5$: C, 59.25; H, 3.73; N, 17.28. Found: C, 59.37; H, 3.61; N, 17.12. TLC $R_f=0.20$ (toluene-ethyl formate-formic acid 5:4:1).

Alternatively, the above procedure can be carried out by utilizing an alkali-metal azide such as sodium, potassium, or lithium azide without the presence of sodium or ammonium chloride.

In a 250 ml Erlenmeyer flask was placed 125 ml of dimethylformamide, 20.4 g (0.05 moles) of 1-(4-cyanophenoxy)-2-formyloxy-3-(2-cyanochromon-5-yloxy)

and 3.3 g (0.05 moles) of sodium azide. The mixture was stirred and heated at 90° C. for 1.5–2 hours; it then was cooled and filtered. The solvent was removed in vacuo and the residue dissolved in water. Then 8 g of sodium carbonate was added, and the aqueous solution was heated at 80° C., for 30 minutes. After cooling the solution to room temperature, 300 ml of acetone was added, and the resulting solution acidified with concentrated sulfuric acid. After distillation of the acetone the residual slurry was cooled in an ice-bath and 1-(4-cyanophenoxy)-2-hydroxy-3-[2-(5-1H-tetrazolyl)-chromon-5-yloxy)]-propane was collected by filtration: 20.4 g (96.4% yeild), m.p. 219°–221° C. TLC: $R_f$=0.20 (toluene-ethyl formate-formic acid 5:4:1).

Example 4
SODIUM 1-(4-CYANOPHENOXY)-2-HYDROXY-3-[2-(5-1H-TETRAZOLYL)CHROMON-5-YLOXY]-PROPANE In a 5.0 L, three-necked flask equipped with a stirrer and reflux condenser were placed 441 g (1.09 moles) of 1-(4-cyanophenoxy-2-hydroxy-3-[2-(5-1H-tetrazolyl)-chromon-5-yloxy]propane, 90.7 g (1.08 moles) of sodium bicarbonate, 1.90 L of methanol, and 1.90 L of tetrahydrofuran. The mixture was stirred and heated at reflux for 5 hours. The hot slurry was filtered and the white product washed with a 50:50 mixutre of methanol and tetrahydrofuran and then with ether: 420 g (90% yield); m.p. 308° C.

Analysis: calculated for $C_{20}H_{14}N_5O_5Na$: C, 56.20; H, 3.30; N, 16.39. Found: C, 55.75; H, 3.23; N, 16.36. TLC $R_f$=0.20 (toluene-ethyl formate-formic acid 5:4:1).

Example 5
ANTI-ALLERGIC ACTIVITY

Compounds described in above examples 3 and 4 were evaluated for anti-allergic activity in the rat by the passive cutaneous anaphylaxis test (hereafter PCA), utilizing egg albumin as the antigen.

PCA is an experimentally induced allergic reaction which develops in the skin of test animals after intravenous injection of an antigen. The intensity of such PCA reactions is assessed by measuring the diameters of wheals which develop in the skin of the test animals. Details of the PCA test can be found in the following references: I. Mota, Life Sciences, 1: 465 (1963); and B. Ogilvie, Immunology, 12: 113 (1967).

In the following table, ID50 is the dose which reduced the diameter of the wheal by 50% when injected intravenously together with the antigen. LD50 is the intravenous dose that caused death in 50% of the test animals. Therapeutic index is the ratio, LD50/ID50. The reference compounds utilized were: disodium chromoglycate (DSCG); 1-(phenoxy)-2-hydroxy-3-[2-(5-1H-tetrazolyl)-chromon-5-yloxy]-propane; 1-(4-chloro-phenoxy)-2-hydroxy-3-[2-(5-1H-tetrazolyl)-chromon-5-yloxy]-propane; 1-(4-hydroxy-phenoxy)-2-hydroxy-3-[2-5-1H-tetrazolyl)-chromon-5-yloxy]-propane; 1-(4-propyl-phenoxy)-2-hydroxy-3-[2-5-1H-tetrazolyl)-chromon-5-yloxy]-propane; and sodium 1-(4-cyano-phenoxy)-2-hydroxy-3-(2-carboxy-chromon-5-yloxy)-propane.

TABLE

COMPARISON OF CLAIMED AND REFERENCED COMPOUNDS

| REFERENCE | $R^1$ | $R^2$ | ID50 (i.v.) μmol/kg | LD50 (i.v.) μmol/kg | THERAPEUTIC INDEX |
|---|---|---|---|---|---|
| Augstein | H | —H | 2.25 | >1051 | >467 |
|  | tetrazolyl | —OH | 0.675 | >1263<4952 | >1870<7482 |
|  | tetrazolyl | —Cl | 1.8 | >1.8 | >1 |
|  | tetrazolyl | —C3H7 | >25.0 | >493 | >19.7 |
| Warren | $NaO_2C$ | —CN | 0.75 | 2375 | 3166 |
| DSCG | — | — | 1.7 | 1953 | 1149 |
| This Specification, Examples 3 and 4 | H tetrazolyl | —CN (Ex. 3) | 0.075 | >1182 | >15,760 |
|  | tetrazolyl | —CN (Salt, ex. 4) | 0.075 | >1851<2469 | >24,680<32,920 |

The preceding Table clearly demonstrates the surprising properties of the claimed compounds. The therapeutic index of 1-(4-cyano-phenoxy)-2-hydroxy-3-[2-(5-1H-tetrazolyl)-chromon-5-yloxy]-propane is about 5-times greater than the nearest conger disclosed in Warren, about 15-times greater than DSCG, and from 2.1 to 8.4-times greater than the compounds reported in Augstein. The therapeutic index of the sodium salt of 1-(4-cyano-phenoxy)-2-hydroxy-3-[2-(5-1H-tetrazolyl)-chromon-5-yloxy]-propane is still more superior than any of the prior art compounds.

What is claimed is:

1. A compound selected from the group consisting of 1-(4-cyano-phenoxy)-2-hydroxy-3-[2-(5-1H-tetrazolyl)-chromon-5-yloxy]-propane or a pharmacologically acceptable, non-toxic salt thereof.

2. The compound as in claim 1, 1-(4-cyano-phenoxy)-2-hydroxy-3-[2-(5-1H-tetrazolyl)-chromon-5-yloxy]-propane.

3. The compound as in claim 1, sodium 1-(4-cyano-phenoxy)-2-hydroxy-3-[2-(5-1H-tetrazolyl)-chromon-5-yloxy)]-propane.

4. A method of producing an anti-allergic effect in an individual having an allergic condition, which method comprises:

administering to the individual an effective anti-allergic amount of a compound selected from the group consisting of 1-(4-cyano-phenoxy)-2-hydroxy-3-[2-(5-1H-tetrazolyl)-chromon-5-yloxy]-propane or a pharmacologically acceptable, non-toxic salt thereof.

5. The method as in claim 4, wherein the compound is 1-(4-cyano-phenoxy)-2-hydroxy-3-[2-(5-1H-tetrazolyl)-chromon-5-yloxy]-propane.

6. The method as in claim 4, wherein the compound is 1-(4-cyano-phenoxy)-2-hydroxy-3-[2-(5-1H-tetrazolyl)-chromon-5-yloxy]-propane sodium salt.

* * * * *